United States Patent [19]

Frevel

[11] 4,247,771
[45] Jan. 27, 1981

[54] PARAFOCUSING DIFFRACTOMETER

[75] Inventor: Ludo K. Frevel, Midland, Mich.

[73] Assignees: Karl M. Kadish; Linus K. Frevel; Gordon H. Frevel, all of Midland, Mich.

[21] Appl. No.: 82,872

[22] Filed: Oct. 9, 1979

[51] Int. Cl.³ .............................................. G01N 23/20
[52] U.S. Cl. .................................. 250/273; 250/278; 250/277 CH
[58] Field of Search .................... 250/272, 273, 277 R, 250/277 CH, 278, 279, 274

[56] References Cited
U.S. PATENT DOCUMENTS 3,903,415  9/1975  Holzapfel ............................ 250/272

FOREIGN PATENT DOCUMENTS 2539646  3/1977  Fed. Rep. of Germany ........... 250/272

OTHER PUBLICATIONS

Klug et al., "X-Ray Diffraction Procedures for Polycrystalline and Amorphous Materials", 2nd ed., John Wiley & Sons, N.Y., 1974, pp. 222-225, 232-235.

Primary Examiner—Alfred E. Smith
Assistant Examiner—Carolyn E. Fields

[57] ABSTRACT

A novel parafocusing X-ray diffractometer operates by irradiating a thin ring of fine crystals with a point source of monochromatic X-rays and passing the cone of diffracted X-rays at each focal point through a pinhole to an X-ray sensor, thereby obtaining optimum values for both line intensity and resolution of lines.

6 Claims, 4 Drawing Figures

PARAFOCUSING DIFFRACTOMETER

BACKGROUND OF THE INVENTION

This invention relates to a novel instrument and to a new and advantageous method afforded by that instrument for obtaining the X-ray diffraction data of a polycrystalline powder.

Conventional powder diffractometers or powder cameras register diffraction lines that represent a portion of the cone of diffracted rays emanating from a powder sample irradiated with a beam of monochromated X-rays. In the Debye-Scherrer-Hull technique, a pencil beam of monochromatic X-rays impinges upon a thin cylindrical specimen consisting of a very large number of tiny crystals of 0.001 cm or less diameter. The monochromatic radiation is usually the $K\alpha_1\alpha_2$ doublet obtained by the use of an appropriate filter or a crystal monochromator. The geometrical factors determining the resolution of the lines in a Debye-Scherrer-Hull diffraction pattern are: R, the radius of the camera; r, the radius of the cylindrical sample; h, the length of the sample; $\delta$, the divergence of the impinging X-ray beam; and $\sigma$, the difference between the wavelengths of $K\alpha_1$ and $K\alpha_2$. For a fixed camera radius, the optimum resolution corresponds to the limit as r, h, $\delta$, and $\sigma$ all approach zero. However, under these conditions the exposure times become inordinately long.

For this reason, parafocusing cameras or diffractometers have gained preference. In the Bragg-Brentano configuration, a rectangular flat-faced briquet of powdered sample is irradiated by a divergent beam of monochromatic X-rays and a small portion of the total diffracted radiation is selected by an appropriately placed narrow receiving slit which lets the focused radiation enter a suitable X-ray detector such as a Geiger-Müller counter. During the exposure, the X-ray detector assembly is turned at twice the angular velocity of the turning sample holder in order to maintain parafocusing conditions. For precision measurements of interplanar spacings, the rectangular sample surface must be exactly tangent to the focusing circle at the center of the goniometer circle and must also be sufficiently short to be a good approximation to the parafocusing circle. Moreover, the sample should be very thin, approximately 0.05 mm thick for a sample having a linear absorption coefficient less than 50 cm$^{-1}$. A highly objectionable feature of this flat surface specimen technique is the great tendency to preferred orientation of the crystallites and the resulting distorted relative intensities of the powder reflections.

Three principal disadvantages of conventional X-ray cameras or diffractometers are: (1) only a small fraction of the total diffraction cone for a particular set of interplanar spacings is measured; (2) the accuracy of the interplanar spacing measurements is markedly dependent on the Bragg angle of direction, i.e., $\Delta d/d = -\cot\theta\Delta\theta$ where d is the interplanar spacing in Angstrom units and $\theta$ is the Bragg angle, and (3) the difficulty of achieving random orientation of the powder particles. Additionally, maximum line intensity and optimum resolution of lines in the diffraction pattern cannot both be achieved by known diffractometers. A major object of this invention is to provide a parafocusing powder diffractometer that avoids these disadvantages. Other objects and advantages of the present invention will be apparent from its description which follows.

SUMMARY OF THE INVENTION

A novel parafocusing X-ray diffractometer has now been developed wherein a point source of monochromatic X-rays irradiates a thin ring of finely powdered crystal sample held along the rim of a sample disk and the cone of diffracted X-rays from that ring form a point focus at a pinhole in a suitably disposed plate, the focused X-rays passing through the pinhole to an X-ray sensor, said point source of X-rays, sample disk, pinhole, and sensor disposed in that order along a linear axis, the planes of the sample disk and plate being essentially perpendicular to said axis, and at least two of the point source, sample disk, and plate being synchronously movable along said axis so as to maintain the sample disk equidistant between the point source and the pinhole while varying the distance between said point source and said pinhole.

DETAILED DESCRIPTION

Figure 1:
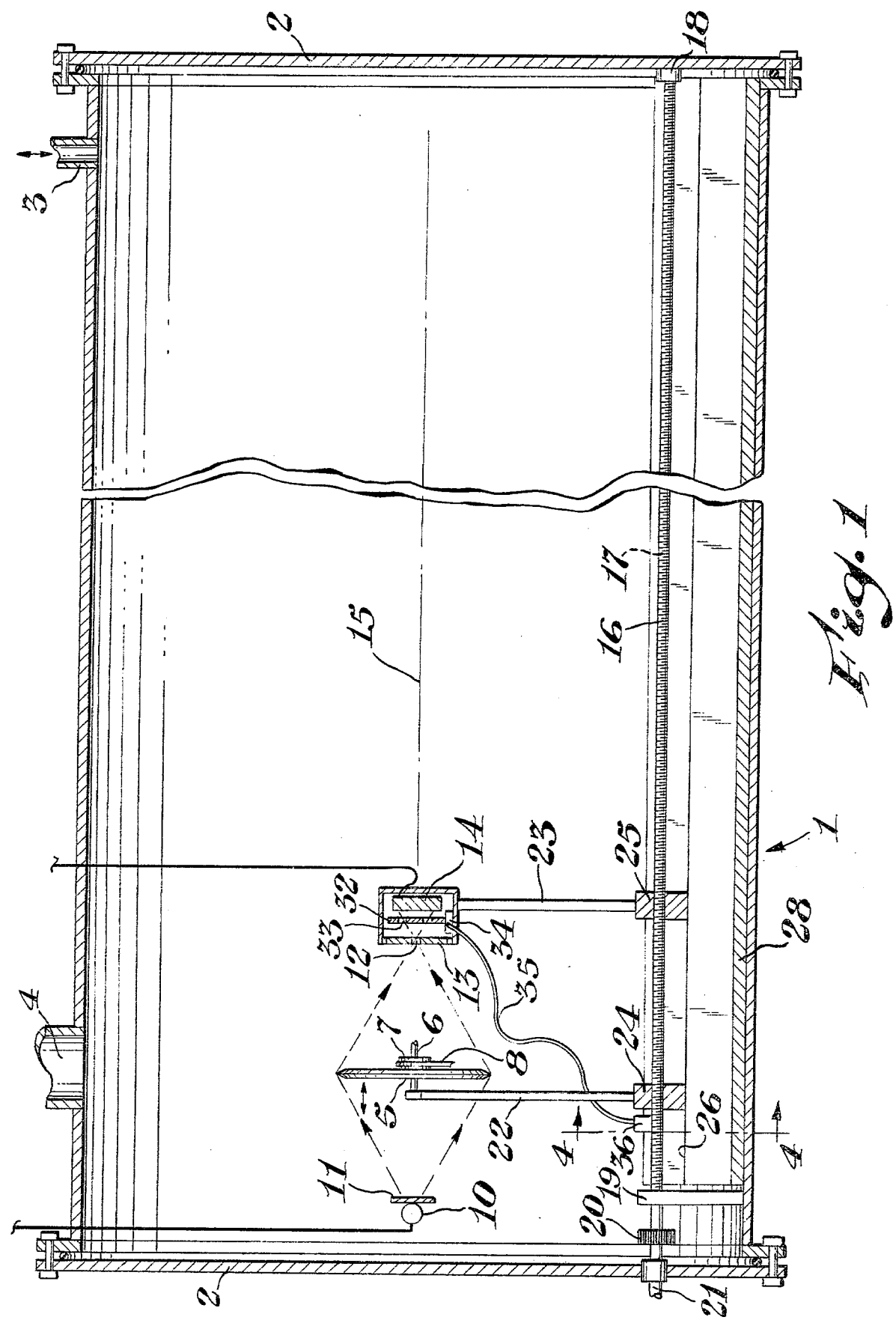
FIG. 1 is an elevation of one mode of the parafocusing apparatus.

Referring to FIG. 1, there is shown one mode of the parafocusing apparatus of the invention as contained in a hollow cylindrical housing (1) closed at each end by removable covers (2). The housing and covers can be made of any convenient strong and rigid material, preferably metal such as steel or brass. The housing has two access ports both normally closed during operation. Evacuation and flushing port (3) provides means for operating the diffractometer after evacuation of air, preferably to about 1 Torr, or in an atmosphere of inert gas such as helium. Sample port (4) provides access to the sample disk (5) which is rotatably mounted on an axle (6) for convenient loading of the edge with a powder sample by rotating the disk with its greased edge in contact with a small pile of powder. Rotation means are shown as consisting of a pulley (7) attached to the disk (5) and a pulley cord (8) activated through the sample port. Alternative geared or frictional means for rotating the sample disk for loading can be used for the purpose.

Figure 2:
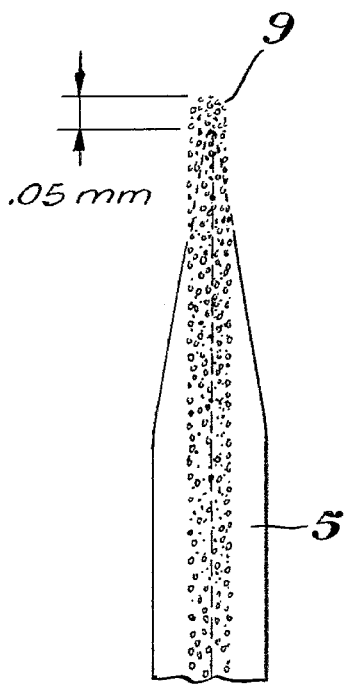
FIG. 2 is a fragmentary side view of the rim of the sample disk having powdered crystals disposed thereon.
Figure 4:
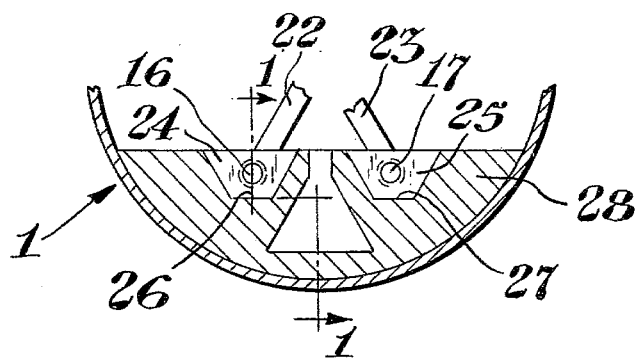
FIG. 4 is a cross-sectional view of the twin guideways and driving elements in the lower part of the apparatus shown in FIG. 1.

The sample disk itself is constructed of a rigid material of very high dimensional stability and preferably having a low coefficient of expansion, for example, tungsten, tantalum, or an alloy such as Invar. The edge of the disk is appropriately thin and is preferably beveled to essentially a knife edge as shown in FIG. 2 so that when greased with petroleum jelly or other such amorphous grease or oil and coated with a powder sample, the adhering rim of powder (9) is of narrow dimensions, suitably about 0.05 mm in thickness. The diameter of the sample disk, which determines the size of the whole apparatus, has practical limits of about 1–10 cm and is preferably about 5 cm, the overall length of the apparatus then being about one meter. As shown in FIG. 1, the X-ray tube (10), the thin filter (11) to provide a monochromatic X-ray beam, the center of the sample disk (5), the pinhole (12) in the plate (13) representing the point focal spot of the diffracted X-rays, and the X-ray sensor (14) are positioned colinearly along or parallel to the long axis (15) of the diffractometer housing (1) with the sample disk (5) exactly equidistant from the X-ray point source (10) and the pinhole (12) in the plate (13). In this mode of the invention, the sample disk (5) and the plate (13) are synchronously movable along the axis (15) by twin lead screw shafts (16, 17) extending longitudinally in parallel, laterally spaced apart relationship along the lower part of the housing (1) and rotatably supported by bearing supports (18) and (19) attached respectively to end cover (2) and the housing wall. As shown in FIG. 4, these lead screw shafts (16, 17) are substantially centered within guideways (26) and (27) defined by bed member (28) lying along the bottom of the housing (1) and they are externally threaded along their lengths except for the surfaces engaged with bearing supports (18) and (19), those external threads mating with internally threaded boxes in support members (24) and (25) sliding within guideways (26) and (27) and holding support 22 for the sample wheel (5) -axle (6) assembly and the support 23 for plate (13) -X-ray sensor (14) assembly respectively. Screw shaft (17) has external threads of exactly twice the pitch of those on screw shaft (16), thereby driving the pinhole (12) -X-ray sensor (14) assembly along a line parallel to the axis (15) of the housing at twice the speed at which the sample disk (5) is simultaneously driven along the same line when the two lead screw shafts (16) and (17) are rotated at the same speed by spur geared connection (20) to a common drive shaft (21) turned by an external motor (not shown). In such a manner, the equal distance (s) between the disk (5) and the focal spot of the diffracted X-rays at the pinhole in the plate (13) is precisely maintained and determinable at each focal setting by an appropriate rotation counter or other measuring device.

In an improved mode of the invention, individual peaks in the focused diffracted X-rays are enhanced by interposing a metal shield (32) with a circular ring slit (33) between plate (13) and the X-ray sensor (14). This ring slit is of dimensions to allow passage of the cone of focused radiation while the metal of shield (32) inside and outside the ring slit screens out unfocused stray radiation. For a parafocusing diffractometer having a sample disk of about 5 cm diameter and an overall length of about a meter as described above, a ring slit (33) of about 25-100 microns uniform width and ring diameter of about 10 mm is appropriate. In a shield (32) of 0.2 mm brass sheet, for example, the central circle of metal can be fixed in place as a spider with multiple thin arms connecting it to the surrounding metal of the shield to define the slit or the central circle of metal and the rest of the metal shield can be separate elements embedded in a sheet of plastic and thereby held in fixed isoplanar relationship to define the ring slit (33).

As shown in FIG. 1, motion of the shield (32) relative to the pinhole (12) -sensor (14) assembly and opposite in direction to maintain alignment of the ring slit (33) with the cone of diffracted X-rays as the sample disk (5) and pinhole (12) -sensor (14) assembly are moved during operation is provided by a looped flexible driveshaft (35) rotated by a geared connection (36) to drive screw (17). The driving end of the driveshaft (35) operates a worm gear-rack mechanism (34) attached to the shield (32). Other equivalent means of gearing the motion of the shield (32) relative to that of the pinhole (12) -sensor (14) assembly can, of course, be employed. The actual speed of the shield (32) and the distance traversed by it are relatively very small, roughly about one fortieth the speed and traverse of the pinhole (12) -sensor (14) assembly.

Satisfactory but somewhat less efficient results are obtained by using a fixed shield (32) having a ring slit (33) of greater slit width to allow passage of the focused cone of diffracted radiation at any position of the elements of the diffractometer during operation. In this mode of the invention, the flexible driveshaft (35) and the geared connections (34) and (36) are not present. However, the synchronously movable shield (32) and narrow ring slit (33) as described give optimum results and are preferred.

Figure 3:
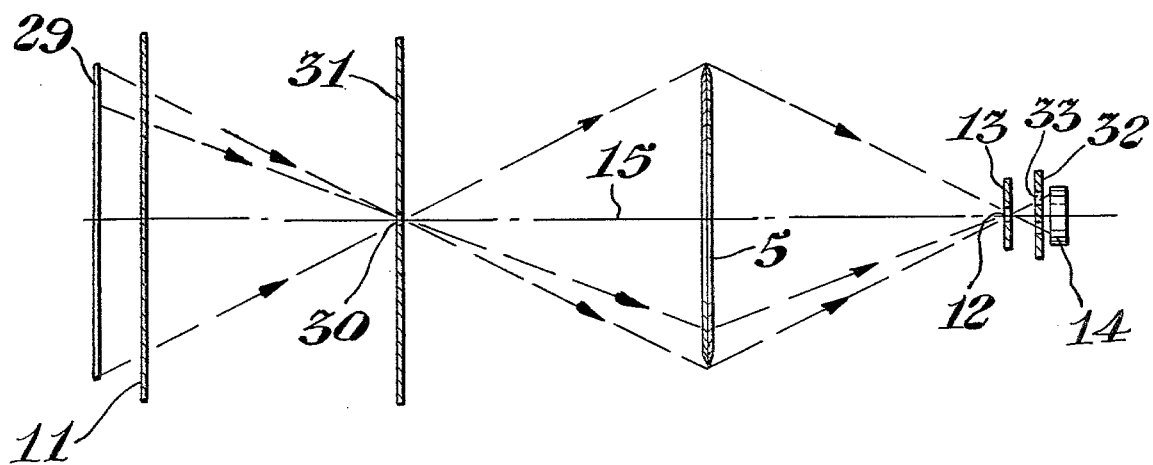
FIG. 3 is a schematic view of elements in another mode of the parafocusing apparatus.

Referring to FIG. 3, another mode of the invention is illustrated wherein an alternative method of obtaining a point source of monochromatic X-rays is used. A flat board disk (29) such as a flat target of an X-ray tube or a Mössbauer source emitting characteristic X-rays from the entire surface is used in conjunction with a pinhole (30) in plate (31) and filter (11) to define a cone of essentially monochromatic X-rays so that the apex of the cone at the pinhole (30) becomes the point source of X-rays. A suitable M,uml/o ssbauer source is a 200-mCiFe$^{57}$ γ-ray having a wavelength of 0.860234 Å. Parafocusing conditions can be maintained in this mode by keeping the X-ray generator (29) and the sample disk (5) stationary but moving the plates with pinholes (30) and (12) along the axis (15) so that they are always on that axis and equidistant from the sample disk (5).

In any mode of this new parafocusing diffractometer, during the traverse of the appropriate elements of the instrument along its longitudinal axis at discrete values of the Bragg angle of the diffracted rays, all of the diffracting crystallites in the powder sample are oriented in such a manner that the normals to their crystallographic planes with interplanar spacing d are perpendicular to the axis and will diffract the filtered WL$\alpha_1$, radiation, for example, in a convergent cone whose apex is at the pinhole (12) in plate (13). The parafocused rays pass through the pinhole (12), and into an X-ray detector or sensor (14) such as a Geiger-Müller counter, a scintillation counter, or a semiconductor detector. For each interplanar spacing d, the Bragg angle is equal to $$\sin^{-1}\left[\frac{\lambda(WL\alpha_1)}{2d}\right]$$

For $\lambda(WL\alpha_2)$ there is a corresponding signal registered with an intensity one tenth that of $\lambda(WL\alpha_1)$. FIG. 2 shows an enlarged cross-sectional view of the edge of sample disk (5). The powder particles, typically of about 50 microns average diameter, adhering to the greased edge may amount to about a quarter million in number for a 5 cm diameter disk so that there is abundant opportunity provided for the various crystallographic planes to be in a reflecting position at their respective Bragg angles. The powder sample is conveniently applied to the greased edge by rotating disk (5) with its edge in contact with a small pile of the powder.

FIG. 1 illustrates a preferred mode of the invention wherein the elements of the diffractometer are enclosed in a housing which can be evacuated for operation in the essential absence of air for better results. The invention is also operable without such a housing and in the presence of air as shown in the example.

EXAMPLE

A parafocusing diffractometer was assembled according to the above-described specifications. As shown in FIG. 1, the X-ray source (10) was a tungsten tube operated at 40 KV with a 25μ focal spot. A brass filter (11) of 0.025 mm thickness was used to screen out WLβ radiation. Finely powdered crystals of pure NaCl having an average diameter of about 50 microns were evenly disposed along the beveled rim of a 5.0 cm diameter tungsten sample disk (5), the thin coating of powder forming a continuous circle held on the rim by a film of petroleum jelly. The sample powder was applied manually using a small camel's hair brush to obtain a uniform coating. The plate member (13) with a pinhole (12) was a plate of 0.2 mm brass sheet having a centrally inset platinum ring with a precision 25 micron diameter circular pinhole. A Geiger-Müller counter with strip chart recorder was used as the X-ray sensor (14). These elements were disposed in the manner shown in FIG. 1 in a modified metalworking flat bed lathe having two V-notched beds, each with a lead screw, one lead screw having threads with twice the pitch of the other. The X-ray tube and filter were fixed in place at one end of the lathe bed while the sample disk and the pinhole-X-ray sensor assemblies were mounted on modified compound rests driven by the two lead screws, the latter assembly being driven by the lead screw with higher pitched threads. The linear distances between the intensity peaks in diffracted X-rays detected by the Geiger-Müller counter and recorded on the strip chart were determined by a calibrated encoder. The apparatus was loosely enclosed within a box having appropriately placed shielding of lead sheet to prevent exposure of the operator to stray radiation.

Using a uniform translation velocity for the sample disk of 2 cm/min. and varying s, the distance between the focal spot of the X-ray tube (10) and the sample disk (5) as shown, the following powder diffraction data were obtained.

TABLE

| hkl | s, mm | $d_{hkl}$, Å | $I_{hkl}/I_{200}$ |
|---|---|---|---|
| 200λ₁ | 126.00 | 2.822 | 0.02 |
| 111α₁ | 107.51 | 3.259 | 0.07 |
| 111α₂ | 106.68 | 3.260 | 0.01 |
| 200α₁ | 92.27 | 2.823 | 1.00 |
| 200α₂ | 91.53 | 2.823 | 0.10 |
| 220α₁ | 62.79 | 1.9956 | 1.20 |
| 220α₂ | 62.27 | 1.9961 | 0.12 |
| 311α₁ | 51.93 | 1.7018 | 0.05 |
| 311α₂ | 51.46 | 1.7019 | <0.01 |
| 222α₁ | 49.19 | 1.6293 | 0.53 |
| 222α₂ | 48.74 | 1.6295 | 0.05 |
| 400α₁ | 40.73 | 1.4112 | 0.32 |
| 400α₂ | 40.31 | 1.4110 | 0.03 | hkl = the Miller indices of a particular powder reflection
$d_{hkl}$ = interplanar crystal spacing in angstrom units
$I_{hkl}$ = peak intensity of the hkl reflection in arbitrary units
$I_{200}$ = peak intensity of the 200 reflection in the same arbitrary units $\lambda(WL\alpha_1) = 1.4764$ Å
$\lambda(WL\alpha_2) = 1.4874$ Å
$\lambda(WL\gamma_1) = 1.0986$ Å

In addition to the NaCl reflections, there appears the 110 reflection (2.239 Å) of tungsten metal from the beveled rim of the sample disk. The half-widths of the 111 reflections (WLα₁ and WLα₂) of NaCl are approximately 0.11 mm at $(I_{111})/2$. The interplanar spacings ($d_{hkl}$) listed in the third column of the table were calculated according to the following equation:

$$d = \frac{\lambda}{2\sin[\tan^{-1} R/s]} = \frac{\lambda\sqrt{R^2 + s^2}}{2R}$$

where R is the radius of the sample disk, s is as previously defined, and λ is the appropriate wavelength.

Contrary to conventional diffractometers or cameras, the accuracy of relatively large interplanar spacings as determined by this new diffractometer is greater than that for small interplanar spacings, e.g.

$$\frac{\Delta d}{d} = \frac{s\Delta s}{R^2 + s^2}$$

$$Lt_{\theta \to 0}\left[\frac{\Delta d}{d}\right] = Lt_{s \to \infty}\left[\frac{s\Delta s}{R^2 + s^2}\right] = 0$$

This feature of the present diffractometer is extremely useful in the identification of complex crystalline solids with large unit cells, for example, crystalline solids such as diphenylsilanediol, hexamethylenetetraselenafulvalene, and perfluorotetracyano-p-quinodimethane. Moreover, the measured intensity for a particular reflection is the sum of all of the diffracted radiation from many crystallites and thus better relative intensities are obtained than are obtainable by the measurement of only a small portion of the diffraction cone as is done by conventional instruments.

I claim:

1. A parafocusing X-ray diffractometer comprising the elements:
   (a) a point source of essentially monochromatic X-rays,
   (b) a circular thin-edged sample disk, said circular disk rotatably mounted at its center on an axle member,
   (c) a flat plate having a pinhole aperture near its center,
   (d) an X-ray sensor, said flat plate and said sensor fixed in spaced apart relationship in an assembly member,
   (e) an essentially cylindrical hollow housing having closed ends and having a sample access port and a flushing port, said point source, axle member, pinhole aperture in the flat shield, and X-ray sensor linearly aligned in that order within said housing and along or parallel to its longitudinal axis, said sample disk perpendicular to said axis and equidistant between said point source and said pinhole aperture, at least two of the elements consisting of said point source, said sample disk, and said assembly member moveable along the said axis of the housing, and
   (f) calibrated means for moving said movable elements along said axis while maintaining said sample disk equidistant between said point source and said pinhole aperture.

2. The diffractometer of claim 1 wherein a flat metal radiation screening member having a circular ring slit is positioned between the flat plate with pinhole aperture and the X-ray sensor in the assembly member.

3. The diffractometer of claim 2 wherein the screening member is synchronously movable with and in opposite direction to the movement of the assembly member.

4. The diffractometer of claim 1 wherein the point source of monochromatic X-rays comprises an X-ray generating tube and a metal filter plate.

5. A method for determining the X-ray diffraction pattern of a powdered crystalline solid which comprises forming an essentially continuous circular ring of said powdered solid, irradiating said ring with a beam of substantially monochromatic X-rays from a point source lying along a line passing through the center of said ring and perpendicular to its plane, adjusting along said line the distance between said point source and said ring, thereby forming multiple cones of diffracted radiation from said ring of powdered solid according to the angle of incidence of said X-rays on said powdered solid, and synchronously moving along said line an X-ray sensor positioned on the side of said ring opposite from said point source, thereby contacting said cones of diffracted radiation with said X-ray sensor and determining the apexes of said cones.

6. The method of claim 5 wherein the cones of diffracted radiation are passed through a ring slit in a metal screening member prior to contacting the X-ray sensor.

* * * * *